United States Patent [19]

Fell et al.

[11] Patent Number: 5,434,312

[45] Date of Patent: Jul. 18, 1995

[54] PROCESS FOR THE HYDROFORMYLATION OF 1,3-BUTADIENE

[75] Inventors: Bernhard Fell; Peter Hermanns, both of Aachen, Germany

[73] Assignee: Hoechst Aktiengesellschaft, Germany

[21] Appl. No.: 300,169

[22] Filed: Sep. 2, 1994

[30] Foreign Application Priority Data

Sep. 9, 1993 [DE] Germany .................. 43 30 489.3

[51] Int. Cl.$^6$ .............. C07C 45/50; C07C 47/02; C07C 47/11; C07C 47/12
[52] U.S. Cl. .................. 568/454; 568/444; 568/452; 568/455; 568/838; 568/883
[58] Field of Search ............. 568/444, 452, 454, 455

[56] References Cited

U.S. PATENT DOCUMENTS

| | | | |
|---|---|---|---|
| 4,426,542 | 1/1984 | Barker et al. | 568/883 |
| 4,740,626 | 4/1988 | Bahrmann et al. | 568/454 |
| 4,996,366 | 2/1991 | Tinucci et al. | 568/455 |
| 5,312,996 | 5/1994 | Pockett | 568/454 |
| 5,382,716 | 1/1995 | Bahrmann et al. | 568/454 |

FOREIGN PATENT DOCUMENTS

| | | |
|---|---|---|
| 33554 | 8/1981 | European Pat. Off. . |
| 366089 | 5/1990 | European Pat. Off. . |
| 2627354 | 12/1976 | Germany . |

*Primary Examiner*—Joseph E. Evans
*Attorney, Agent, or Firm*—Jordan B. Bierman; Bierman and Muserlian

[57] ABSTRACT

1,3-Butadiene is hydroformylated at 60° to 150° C. and 1 to 20 MPa in the presence of an aqueous solution which contains, as catalyst, at least one water-soluble rhodium compound and at least one water-soluble organic phosphine. A pH of 8 to 11 is maintained in the aqueous catalyst solution to increase the selectivity of the reaction with respect to the formation of n-five carbon aldehydes and their secondary products. The latter, in particular, can be hydrogenated to 2-propylheptanol, useful as the alcohol component of phthalic ester plasticizers.

11 Claims, No Drawings

PROCESS FOR THE HYDROFORMYLATION OF 1,3-BUTADIENE

Application claims the benefit of the priority of German Application P 43 30 489.3, filed Sep. 9, 1993.

The invention relates to a process for the hydroformylation of 1,3-butadiene to produce precursors of 2-propylheptanol and other valuable products.

BACKGROUND OF THE INVENTION

Primary monohydric alcohols having 8 to 10 carbon atoms, esterified with phthalic acid, are used to a great extent as plasticizers, in particular for polyvinyl chloride. Alcohols having shorter carbon chains give plasticizers having a good gelling power, but their higher volatility is a disadvantage. Phthalic esters of longer-chain alcohols lead to plasticizers which gel slowly and have poorer cold stability.

The properties of the phthalic ester plasticizers are determined not only by the length, but also by the branching, of the carbon chain in the alcohol molecule. Alcohols having a low degree of branching give ester plasticizers which are highly prized because of their high cold flexibility. Substantially linear alcohols having 8 to 10 carbon atoms in the molecule are therefore gaining increasing importance as the alcohol component. A precondition for their use is that they be inexpensive and available in large quantities. Currently, 2-ethylhexanol is the most important alcohol component for phthalic esters; however, attempts are being made to find further raw material bases for the preparation of alcohols having the desired properties.

According to DE-C-2,855,421, phthalates of nine carbon alcohols, used as plasticizers, are obtained by oxo-reaction of eight carbon olefins, hydrogenation of the reaction product, and esterification of the resultant alcohols with phthalic anhydride. There are certain requirements of the starting olefins. They should comprise 3% to 20% by weight of compounds having an isobutane skeleton, and less than 3% by weight of compounds having a quaternary carbon atom. More than 90% by weight of the total amount of the olefins should be present as n-octenes, monomethylheptenes, and dimethylhexenes. Finally, the weight ratio of the total amount of n-octenes and monomethylheptenes to dimethylhexenes should be greater than 0.8.

Phthalic esters of ten carbon alcohols are the subject matter of European Patent Application 03 66 089. The alcohols are used in the form of a mixture which is obtained by hydroformylation of a butene fraction, aldol condensation of the resulting aldehyde mixture, and subsequent hydrogenation.

Another way to obtain didecyl phthalate mixtures is described in European Patent Application 04 24 767. The esters are prepared by a multi-stage process comprising dimerization of butene mixtures, hydroformylation and hydrogenation of the resulting octene mixture to give a nonanol mixture, dehydration of the nonanol mixture to form a nonene mixture, and hydroformylation and hydrogenation of the nonene mixture to a mixture of decanols.

The known processes still do not fulfill all the economic and technical requirements of such a process to be carried out on an industrial scale, because the starting materials are not available in sufficient quantity, are not available at a reasonable price, and/or the conversion of the starting material into the alcohols is too complex.

SUMMARY OF THE INVENTION

It is, therefore, an object of the invention to develop a process which, starting from inexpensive raw materials, provides a technically simple approach to the desired alcohols and, in some cases, further valuable materials.

The invention consists of a process for the hydroformylation of 1,3-butadiene at temperatures of 60° to 150° C. and pressures of 1 to 20 MPa in the presence of an aqueous solution which contains at least one rhodium compound and at least one water-soluble organic phosphine. The process comprises reacting the butadiene at a pH in the aqueous solution of 8.0 to 11.0. The starting 1,3-butadiene is a necessary by-product of the preparation of ethylene by thermal cracking of light petroleum and higher hydrocarbons. It is isolated from the four-carbon cracking cuts of the pyrolysis product, e.g. by liquid-liquid extraction with a selective solvent such as acetonitrile, dimethylformamide, or n-methylpyrrolidone. In addition to this, it can easily be obtained by dehydrogenation of butane or butene.

DETAILED DESCRIPTION OF THE INVENTION

To carry out the hydroformylation, 1,3-butadiene is used in its currently commercial form, i.e. a purity of at least 99.5% by weight. The hydroformylation of the conjugated diolefin has already been performed several times. It proceeds both under the influence of cobalt catalysts and rhodium catalysts. The cobalt-catalyzed reaction is described e.g. by Adkins and Williams (J. Org. Chem. 17, 980 (1952) and leads, in moderate yield, to a mixture of n- and i-valeraldehydes in a molar ratio of 1:1.

More favorable aldehyde yields are achieved in the hydroformylation of 1,3-butadiene in the presence of rhodium catalysts. Complex compounds of rhodium with a multidentate ligand which contains trivalent phosphorus atoms have proven useful. A process based on such catalysts is described, e.g. in EP-B-33 554.

In the context of the present invention, the hydroformylation of the 1,3-butadiene is carried out in a heterogeneous two-phase system. The principles of this process are described, e.g. in DE-C-26 27 354. The process is characterized by the introduction of an organic phase, which contains the starting olefin and the reaction product, and an aqueous phase, in which the catalyst is dissolved. Catalysts which are used are water-soluble rhodium complex compounds with water-soluble, organic phosphines as ligands. The water-soluble phosphines include, in particular, trialkylphosphines, triarylphosphines, tri(alkyl, aryl)phosphines, alkylenediphosphines, and aryldiphosphines which contain at least one organic radical substituted by a sulfonic acid group or a carboxyl group. Their preparation is known, cf. e.g. DE-C-26 27 354 and DD-A-259 194. Compounds which are particularly suitable are triphenylphosphine mono-, triphenylphosphine di- and triphenylphosphine trisulfonates which can be used as individual compounds or as a mixture of 2 or 3 sulfonate components.

Surprisingly, in accordance with the new procedure, by maintaining a pH of 8.0 to 11.0 in the aqueous phase during the reaction, the selectivity of the reaction with respect to formation of five carbon aldehydes and secondary products of the five carbon aldehydes is successfully markedly increased. The secondary products of the five carbon aldehydes which result from the hydroformylation include, as intermolecular condensation products, unsaturated ten carbon aldehydes which can be hydrogenated to form 2-propylheptanol. A further secondary product is the intramolecular condensation product of 1,6-hexanedial which, after elimination of water and addition of hydrogen, gives cyclopentanecarbaldehyde and, after hydrogenation, cyclopentanemethanol, a valuable intermediate for organic synthesis. It has proven to be particularly useful to work at pH's in the range from 8.5 to 9.5.

The pH's which are a feature of the process according to the invention relate to the aqueous phase during the reaction, i.e. essentially to the solution of the catalyst comprising rhodium and water-soluble organic phosphine. The pH is determined in a known manner, e.g. with the aid of a hydrogen electrode.

The pH is adjusted by addition of basic reagents to the conventionally weakly alkaline to weakly acidic catalyst solution. Compounds which are suitable for this include alkali metal hydroxides, alkali metal carbonates, ammonia, and amines. If the alkalinity of the solution exceeds the pH range to be maintained, inorganic acids, such as phosphoric acid or sulfuric acid; acid salts of polyvalent inorganic acids such as alkali metal hydrogen sulfate or water-soluble organic acids, e.g. formic acid, acetic acid, and propionic acid, are added to the solution until the desired pH is achieved. It has also proven to be useful to use buffer solutions which permit a precise adjustment of the pH range and ensure its constancy over long reaction periods. Depending on the pH's required, suitable buffer mixtures are, e.g., borax-HCl, borax-NaOH, NaHCO$_3$—NaOH, H$_3$BO$_3$/KCl-NaOH.

The activity of the catalyst present in the alkaline solution is not impaired, although, in the opinion of those skilled in the art, the presence of rhodiumhydridocarbonyls is decisive for the catalytic activity. Nor does the pH have any effect on the rate and extent of the reaction of butadiene; the total amount of resulting five and ten carbon aldehydes remains about the same. Only the ratio of five carbon aldehydes to ten carbon aldehydes is shifted in favor of the latter with the increase in pH. However, when catalyst solutions having a pH above 11 are used, the formation of the ten carbon product markedly decreases.

The catalyst solution can be preformed and then added to the reaction system. However, with equally good results, it can also be prepared in the reaction mixture under reaction conditions from rhodium or at least one rhodium compound and an aqueous solution of at least one water-soluble organic phosphine. In addition to metallic rhodium in finely divided form, the rhodium source can be water-soluble rhodium salts such as rhodium chloride, rhodium sulfate, rhodium acetate, or compounds which are sparingly soluble in water or water-insoluble, such as rhodium 2-ethylhexanoate or rhodium oxides. Not only rhodium and rhodium compounds, but also the water-soluble phosphines, can be used as pure substances or as mixtures of two or more components.

The rhodium concentration in the aqueous catalyst solution is 20 to 2,000 ppm by weight, preferably 50 to 700 ppm by weight, based on the aqueous catalyst solution. Per mole of rhodium, 4 to 100 mol of phosphorus is used in the form of water-soluble phosphines. Phosphine/rhodium mol ratios above 15:1 repress the formation of the branched primary product and favor the production of dialdehyde. The phosphine/rhodium ratio also has an influence on the formation of ten carbon aldehydes. Below a molar ratio of P/Rh of 30:1, the aldol condensation products are formed only to a slight extent. The total amount of unbranched monoaldehyde and its intermolecular aldol condensation product is scarcely influenced by the P/Rh ratio.

The hydroformylation of the 1,3-butadiene proceeds at temperatures between 60° and 150° C, preferably 90° and 120° C. Higher temperatures within the range favor the formation of dialdehyde. Above about 120° C., the formation of five carbon aldehydes and their intermolecular aldol condensation products decreases.

The hydroformylation of 1,3-butadiene is preferably carried out at pressures of 1 to 10 MPa. Lower pressures within this range preferentially lead to the formation of five carbon aldehydes, but impair the conversion rate. Pressures above 10 MPa promote the aldol condensation.

The conversion of butadiene per unit time and the condensation of five carbon aldehydes to form ten carbon aldehydes is significantly increased if a phase transfer reagent (solubilizer) is added to the aqueous alkaline catalyst solution. It alters the physical properties of the interfaces between the two liquid phases and facilitates the transfer of the organic reactants into the aqueous catalyst phase.

Known solubilizers comprise compounds having hydrophilic groups which are ionic (anionic or cationic) or nonionic. The anionic compounds include sodium salts, potassium salts, or ammonium salts of carboxylic acids having 8 to 20 carbon atoms, in particular of saturated fatty acids having 12 to 18 carbon atoms; also useful are alkyl sulfates, alkylbenzenesulfonates, and alkylbenzenephosphates. Examples of cationic solubilizers are tetraalkylammonium and N-alkylpyridinium salts. The nonionic phase transfer reagents cannot dissociate into ions in aqueous solution; these include alkyl polyethylene glycols, alkylphenyl polyethylene glycols, alkylolamides of fatty acids, and trialkylamine oxides. Finally, ampholytes such as aminocarboxylic acids, betaines, and sulfobetaines are also useful as solubilizers.

In particular, cationic solubilizers of the formula [A-N($R^1R^2R^3$)]$^+$E$^-$ have proven useful, in which A is a straight or branched chain alkyl radical having 6 to 25 carbon atoms $R^1$, $R^2$, $R^3$ are the same or different straight or branched alkyl radicals having 1 to 5 carbon atoms, and E is an anion. In particular, sulfate, tetrafluoroborate, acetate, methosulfate, benzene sulfonate, alkylbenzenesulfonate, toluenesulfonate, lactate, and citrate are suitable as the anion.

The reaction mixture resulting from the hydroformylation is separated from the catalyst by simple phase separation. The aqueous catalyst solution can, if required after regeneration and adjustment of the rhodium and/or phosphine concentration, be reused. The organic phase is separated by distillation into the constituents which are used as such or further processed. The ten carbon aldehyde fraction can be hydrogenated directly to form 2-propylheptanol. The five carbon aldehydes are preferably converted to aldols as a mixture. The reaction proceeds in the conventional manner under the influence of basic catalysts. Catalysts which may be used include alkali metal carbonates or alkali metal hydroxides, in particular compounds of sodium or of potassium and amines, preferably tertiary amines, such as triethylamine, tri-n-propylamine, and tri-n-butylamine.

Temperatures of 60° to 160° C. in particular 80° to 130° C. and atmospheric pressure or elevated pressure up to about 1 MPa are employed. The reaction time is from a few minutes up to several hours and is dependent, in particular, on the catalyst type and reaction temperature. Because of their relatively high reaction rates, n-5 carbon aldehydes, especially, dimerize with themselves or with isomeric five carbon aldehydes to give ten carbon aldehydes; in contrast, condensation of the branched 5 carbon aldehydes among themselves is insignificant. The isomeric ten carbon aldehydes are hydrogenated to give the corresponding saturated alcohols.

Hydrogenation catalysts which are suitable for this reaction are those based on nickel, chromium, or copper. Conventionally, the hydrogenation temperature is between 100° and 180° C., and the pressure is between 1 and 10 MPa. The mixture of isomeric ten carbon alcohols is distilled to purify it. Whether coming directly from the hydroformylation stage or from the aldol condensation of the five carbon aldehydes, they are quite suitable as the alcohol component in phthalic esters which are used as plasticizers. The preparation of such phthalic esters is known [cf. Ullmann, Encyclopädie der Technischen Chemie [Encylopaedia of Industrial Chemistry] (1979), Vol. 18, page 536 ff.].

For example, phthalic anhydride is expediently reacted with the decyl alcohol mixture in a single stage in a molar ratio 1:2. The reaction rate can be increased by the use of catalysts and/or by raising the reaction temperature. In order to shift the equilibrium in the direction of ester formation, it is necessary to remove the water formed from the reaction mixture.

The following Examples describe the invention, but it is not restricted to the embodiments described.

The procedure is carried out in all Examples in the same manner. Into a 125 ml stainless steel autoclave, are introduced, in an argon atmosphere, 40 g of an aqueous catalyst solution which contains 16.4 mg of rhodium (in the form of rhodium 2-ethylhexanoate or rhodium sulfate, equivalent to 410 ppm of Rh) and varying amounts of tris(m-sulfonatophenyl)phosphine trisodium salt. The pH thereof, unless otherwise stated, is adjusted by addition of sodium carbonate or sulfuric acid. The catalyst solution is treated at 110° C. and 10 MPa for 90 minutes with synthesis gas (volume ratio $CO/H_2$=1:1). 20 g of 1,3-butadiene is added in each case to the preformed catalyst, the desired reaction pressure is adjusted using synthesis gas, and the mixture is allowed to react for 12 hours. After completion of the reaction, the catalyst and product phases are separated. The catalyst phase is extracted three times, each time with 15 ml of ether. The product phase and ether extract are combined, dried by sodium sulfate, and hydrogenated at 140° C. and 20 MPa for 12 hours in the presence of a Pt-activated charcoal catalyst (10% by weight of Pt). The hydrogenation product is analyzed by gas chromatography.

In the examples, the following abbreviations are used:
n-pentanol n-P
2-methylbutanol 2-MB
cyclopentanemethanol CPM
2-propylheptanol PH

Example 1

Reaction conditions: 120° C.; 20 MPa; aqueous/organic phase (by vol.)=2:1; $CO/H_2$ (by vol.)=1:1; pH of the aqueous phase: 9.

| Experiment | P:Rh (in moles) | n-P (% by weight) | 2-MB (% by weight) | CPM (% by weight) | PH (% by weight) | (n-P + PH) (% by weight) |
| --- | --- | --- | --- | --- | --- | --- |
| 1/1 | 15:1 | 45 | 4 | 7 | 9 | 54 |
| 1/2 | 30:1 | 48 | 5 | 9 | 10 | 58 |
| 1/3 | 40:1 | 48 | 4 | 8 | 13 | 61 |
| 1/4 | 60:1 | 38 | 4 | 7 | 20 | 58 |
| 1/5 | 80:1 | 42 | 3 | 8 | 18 | 60 |

Example 2

Reaction conditions: 120° C.; 20 MPa; P/Rh (in moles)=60:1; aqueous/organic phase (by vol.)=2:1; $CO/H_2$ (by vol.)=1:1.

| Experiment | pH | n-P (% by weight) | 2-MB (% by weight) | CPM (% by weight) | PH (% by weight) | (n-P + PH) (% by weight) |
| --- | --- | --- | --- | --- | --- | --- |
| 2/1 | 3 | 61 | 4 | 8 | 7 | 68 |
| 2/2 | 7 | 47 | 3 | 9 | 8 | 55 |
| 2/3 | 9 | 36 | 3 | 8 | 23 | 60 |
| 2/4 | 11 | 55 | 4 | 8 | 11 | 66 |

Example 3

Reaction conditions: 20 MPa; P/Rh (in moles)=60:1; aqueous/organic phase (by vol.)=2:1; $CO/H_2$ (by vol.)=1:1; pH of the aqueous phase: 9.

| Experiment | Temperature (°C.) | n-P (% by weight) | 2-MB (% by weight) | CPM (% by weight) | PH (% by weight) | (n-P + PH) (% by weight) |
| --- | --- | --- | --- | --- | --- | --- |
| 3/1 | 100 | 31 | 2 | 5 | 27 | 58 |
| 3/2 | 120 | 36 | 3 | 8 | 23 | 59 |
| 3/3 | 140 | 29 | 3 | 8 | 7 | 36 |

Example 4

Reaction conditions: 120° C.; P/Rh (in moles)=60:1; aqueous/organic phase (by vol.)=2:1; pH of the aqueous phase: 9.

| Experiment | Pressure (MPa) | n-P (% by weight) | 2-MB (% by weight) | CPM (% by weight) | PH (% by weight) | (n-P + PH) (% by weight) |
| --- | --- | --- | --- | --- | --- | --- |
| 4/1 | 4.0 | 57 | 2 | 12 | 8 | 65 |
| 4/2 | 6.0 | 67 | 4 | 10 | 10 | 77 |

-continued

| Experiment | Pressure (MPa) | n-P (% by weight) | 2-MB (% by weight) | CPM (% by weight) | PH (% by weight) | (n-P + PH) (% by weight) |
|---|---|---|---|---|---|---|
| 4/3 | 8.0 | 55 | 3 | 9 | 13 | 68 |
| 4/4 | 12.0 | 49 | 4 | 8 | 18 | 67 |
| 4/5 | 16.0 | 28 | 2 | 6 | 23 | 51 |
| 4/6 | 20.0 | 36 | 3 | 8 | 23 | 59 |
| 4/7 | 26.0 | 52 | 3 | 8 | 15 | 67 |

Example 5

Reaction conditions: 100° C; 5.5 MPa; P/Rh (in moles)=60:1; aqueous/organic phase (by vol.)=2:1; $CO/H_2$ (by vol.)=1:1.

| Experiment | pH | n-P (% by weight) | 2-MB (% by weight) | CPM (% by weight) | PH (% by weight) | (n-P + PH) (% by weight) |
|---|---|---|---|---|---|---|
| 5/1 | 9 | 33 | 2 | 4 | 25 | 58 |
| 5/2 | 9 | 26 | 2 | 4 | 32 | 58 |
| 5/3 | 11 | 49 | 2 | 1 | 19 | 68 |
| 5/4 | 11 | 53 | 2 | 1 | 22 | 75 |

The results of these experiments show that the selectivity of the reaction for the aldolization product 2-propylheptenal is satisfactorily high even at pressures around 5 MPa. The selectivity for the aldol condensation product decreases on transferring from the weakly alkaline to the more strongly alkaline region.

Example 6

Reaction conditions: 100° C.; 5.5 MPa; P/Rh (in moles)=60:1; aqueous/organic phase (by vol.)=2:1; $CO/H_2$ (by vol.)=1:1; pH of the aqueous phase: 9 (adjusted in Experiments 6/2 to 6/4 with the aid of an $H_3BO_3$/KCl-NaOH buffer); DTAB: dodecyltrimethylammonium bromide.

| Experiment | Surfactant | Buffer | n-P (% by weight) | 2-MB (% by weight) | CPM (% by weight) | PH (% by weight) | (n-P + PH) (% by weight) |
|---|---|---|---|---|---|---|---|
| 6/1 | DTAB | — | 24 | 2 | 8 | 20 | 44 |
| 6/2 | — | + | 27 | 2 | 4 | 19 | 46 |
| 6/3 | — | + | 32 | 2 | 5 | 18 | 50 |
| 6/4 | DTAB | + | 22 | 3 | 7 | 29 | 51 |

The results show that the selectivity of the reaction with respect to formation of linear five carbon aldehyde and its aldol condensation secondary product decreases if the procedure is carried out with the addition of surfactant or buffer mixtures.

The experiments below show the increases of the conversion/unit of time when a surfactant is added to the catalyst solution

| Reaction time/h | Pressure drop/MPa | |
|---|---|---|
| | without surfactant | with addition of surfactant |
| 1 | 0.7 | 2.0 |
| 2 | 1.3 | 3.1 |
| 4 | 2.8 | 4.9 |
| 8 | 4.3 | 6.0 |
| 12 | 5.1 | 6.3 |

Example 7 (comparison)

This comparative example shows that 1-butene behaves completely differently from 1,3-butadiene in the hydroformylation under the conditions according to the invention. The hydrogenated reaction product chiefly comprises n-pentanol and only contains 2-propylheptanol in very minor amounts.

Reaction conditions: 100° C.; 5.5 MPa; P/Rh (in moles)=60:1; aqueous/organic phase (by vol.)=2:1; $CO/H_2$ (by vol.)=1:1; pH of the aqueous phase: 9.

| Experiment | n-P (% by weight) | 2-MB (% by weight) | PH (% by weight) |
|---|---|---|---|
| 7/1 | 91 | 4 | 1 |
| 7/2 | 93 | 4 | 0.4 |

While only a limited number of specific embodiments of the present invention have been expressly set forth, it is, nonetheless, to be broadly construed, and not to be limited except by the character of the claims appended hereto.

What is claimed is:

1. A process for the hydroformylation of 1,3-butadiene at a reaction temperature of 60° to 150° C. and a reaction pressure of 1 to 20 MPa in the presence of a catalyst, said catalyst comprising an aqueous solution containing rhodium or at least one rhodium compound and at least one phosphine, said solution having a pH of 8.0 to 11.0.

2. The process of claim 1 wherein said pH is 8.5 to 9.5.

3. The process of claim 1 wherein said pH is adjusted with the aid of a buffer.

4. The process of claim 1 wherein said temperature is 90° to 120° C.

5. The process of claim 1 wherein said pressure is 1 to 10 MPa.

6. The process of claim 1 wherein said rhodium is present in said solution in a concentration of 20 to 2000 ppm by weight, based on said solution.

7. The process of claim 6 wherein said concentration is 50 to 700 ppm by weight.

8. The process of claim 1 wherein, per mol of said rhodium, 4 to 100 mol of phosphorus is present in said solution.

9. The process of claim 8 wherein, per mol of said rhodium, 10 to 60 mol of phosphines is present in said solution.

10. The process of claim 1 wherein said water-soluble phosphine is selected from the group consisting of triarylphosphines, trialkylphosphines, tri(alkylaryl)phosphines, alkylenediphosphines, and aryldiphosphines, each containing at least one sulfonic acid group or at least one carboxyl group.

11. The process of claim 1 wherein said solution contains a solubilizer.

* * * * *